United States Patent [19]
Kay

[11] Patent Number: 4,766,132
[45] Date of Patent: Aug. 23, 1988

[54] AROYLAMINOMETHYLPYRIDINES, COMPOSITION CONTAINING THEM, AND METHOD OF COMBATTING FUNGI USING THEM

[75] Inventor: Ian T. Kay, Wokingham, England

[73] Assignee: Imperial Chemical Industries PLC, London, England

[21] Appl. No.: 823,751

[22] Filed: Jan. 29, 1986

[30] Foreign Application Priority Data

Feb. 26, 1985 [GB] United Kingdom ............... 8504871

[51] Int. Cl.$^4$ ............... A01N 43/40; C07D 213/57; C07D 401/12
[52] U.S. Cl. ............... 514/332; 514/335; 514/357; 546/261; 546/262; 546/283; 546/284; 546/329; 546/330; 546/331; 546/332; 546/335; 546/336; 546/337; 71/90; 71/94
[58] Field of Search ............ 546/329, 330, 334, 335, 546/337, 357, 262, 261, 283, 284, 330, 331, 332, 336; 514/332, 335

[56] References Cited
U.S. PATENT DOCUMENTS
4,501,746 2/1985 Krumkalns ............... 514/357
4,515,959 5/1985 Kay et al. ............... 548/378

FOREIGN PATENT DOCUMENTS
1595861 12/1969 Denmark ............... 546/336
129433 12/1984 European Pat. Off. ........... 514/357

Primary Examiner—Mary C. Lee
Assistant Examiner—Kurt G. Briscoe
Attorney, Agent, or Firm—Cushman, Darby & Cushman

[57] ABSTRACT

Compounds of formula:

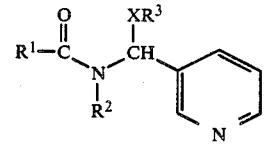

and stereoisomers thereof, wherein $R^1$ is unsubstituted or substituted aryl or heteroaryl; $R^2$ is H, alkyl, alkenyl or alkynyl; X is O, NH, or S; $R^3$ being alkyl, alkenyl, alkynyl or $COR^4$ where $R^4$ has an $R^3$ value, when X is O; $R^3$ being —CO— alkyl when X is NH; and $R^3$ being alkyl, alkenyl or $CSNR^5R^6$ where $R^5$ and $R^6$, which may be the same or different, are H, alkyl, alkenyl or, together with the adjacent N atom, constitute a ring, when X is S; or $XR^3$ together represent —CN; and salts and metal complexes thereof, have fungicidal and plant growth regulating activity.

6 Claims, No Drawings

AROYLAMINOMETHYLPYRIDINES, COMPOSITION CONTAINING THEM, AND METHOD OF COMBATTING FUNGI USING THEM

This invention relates to heterocyclic compounds useful as fungicides and plant growth regulators, to processes for preparing them, to fungicidal and plant growth regulating compositions containing them, and to methods of combating fungi, especially fungal infections in plants, and to methods of regulating the growth of plants.

The invention provides compounds having the general formula (I):

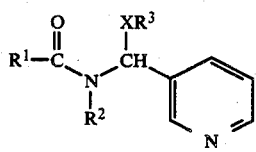
(I)

and stereoisomers thereof, wherein $R^1$ is aryl or heteroaryl, both of which may be substituted or unsubstituted; $R^2$ is H, $C_{1-6}$ alkyl, $C_{1-6}$ alkenyl, or $C_{1-6}$ alkynyl; X is O, NH, or S; provided that when X is O, $R^3$ is $C_{1-6}$ alkyl, $C_{1-6}$ alkenyl, $C_{1-6}$ alkynyl, or $COR^4$ where $R^4$ is as defined for $R^3$, and that when X is NH, $R^3$ is —CO—$C_{1-6}$ alkyl; and that when X is S, $R^3$ is $C_{1-6}$ alkyl, $C_{1-6}$ alkenyl or $CSNR^5R^6$ where $R^5$ and $R^6$, which may be the same or different are H, $C_{1-6}$ alkyl or $C_{1-6}$ alkenyl or together constitute a ring; or $XR^3$ together represent —CN; and salts and metal complexes thereof.

The compounds of the invention may contain chiral centres. Such compounds are generally obtained in the form of racemic mixtures. However, these and other mixtures can be separated into the individual isomers by methods known in the art, and this invention embraces such isomers.

Preferred alkyl groups for $R^2$ or $R^3$ contain from 1 to 6, especially 1 to 4, carbon atoms. When $R^2$ is alkyl it can be a straight or branched chain alkyl group having 1 to 6, e.g. 1 to 4 carbon atoms; examples are methyl, ethyl, propyl (n- or iso-propyl) and butyl (n-, sec-, iso- or t-butyl). When $R^3$ is alkyl it is preferably an alkyl group containing from 1 to 3 carbon atoms e.g. methyl, ethyl, propyl (n or iso-propyl). $R^3$ is most preferred as methyl. Preferred cycloalkyl groups for $R^2$ are cyclopropyl, cyclobutyl, cyclopentyl, and cyclohexyl. Preferred alkenyl and alkynyl groups for $R^2$ contain up to 6 carbon atoms; and include allyl and propargyl.

When $R^1$ is aryl, e.g. phenyl, it may be unsubstituted, or substituted with 1,2 or 3 ring substituents, which may be the same or different. Examples of aryl groups for $R^1$ are phenyl, 2-, 3-, or 4-chlorophenyl, 2,4-dichlorophenyl, 2,4-difluorophenyl, 2-, 3- or 4-fluorophenyl, 2-, 3- or 4-bromophenyl, 2-, 3- or 4-methoxyphenyl, 2,4-dimethoxyphenyl, 2-, 3- or 4-ethoxy-phenyl, 2-fluoro-4-chlorophenyl, 2-chloro-4-fluorophenyl, 2-, 3- or 4-methylphenyl, 2-, 3- or 4-ethylphenyl, 2-, 3-or 4-trifluoromethylphenyl, 4-phenylphenyl (4-biphenyly), 4-chloro-2methoxyphenyl, 4-fluoro-2-methoxyphenyl, 4-chloro-2-nitrophenyl, 2-fluoro-4-methylphenyl, 4-isopropylphenyl. A preferred value for $R^1$ is 2,4-dichlorophenyl.

When $R^1$ is heteroaryl (i.e. heteroaromatic), it may be, for example, a thiophene, furan or pyridine group, which may be unsubstituted or substituted. Suitable substituents include, for example, those defined above for the aryl, e.g. phenyl, moiety of $R^1$.

X is preferably oxygen.

The present invention includes salts, and metal complexes, of the above defined compounds.

In a preferred aspect the present invention provides compounds having the formula:

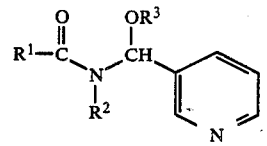

and stereoisomers thereof, wherein $R^1$ is alkyl or heteroaryl, both optionally substituted; $R^2$ is $C_{1-6}$ alkyl, $C_{1-6}$ alkoxy $C_{1-6}$ alkyl, cycloalkyl, $C_{1-6}$ alkenyl or $C_{1-6}$ alkynyl; and $R^3$ is $C_{1-3}$ alkyl.

In a further aspect the invention provides compounds having the general formula:

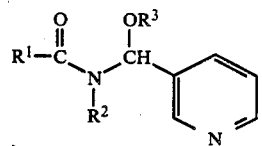

and stereoisomers thereof, wherein $R^1$ is aryl or heteroaryl, both optionally substituted; $R^2$ is $C_{1-6}$ alkyl, $C_{1-6}$ alkoxy $C_{1-6}$ alkyl, cycloalkyl, $C_{1-6}$ alkenyl or $C_{1-6}$ alkynyl; and $R^3$ is $C_{1-3}$ alkyl; and salts and metal complexes thereof.

In a still further aspect the invention provides compounds as defined above wherein $R^1$ is furyl or phenyl substituted with halogen, nitro, trifluoromethyl or alkoxy; $R^2$ is $C_{1-6}$ alkyl, allyl, methoxyethyl, propargyl, or $C_{3-6}$ cycloalkyl; and $R^3$ is methyl.

In a more preferred aspect the invention provides compounds as defined above wherein $R^1$ is 4-chlorophenyl or 2,4-dichlorophenyl, especially the latter.

Examples of the compounds of the invention are shown in Table I below in which X is oxygen and the different values for $R^1$, $R^2$ and $R^3$ are displayed.

TABLE I

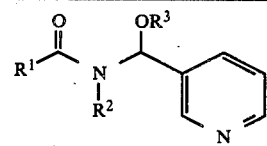

| COMPOUND NO. | $R^1$ | $R^2$ | $R^3$ | M.p.t. (°C.) |
|---|---|---|---|---|
| 1 | 2,4-$Cl_2C_6H_3$ | $CH_3$ | $CH_3$ | 68–71 |
| 2 | 2,4-$Cl_2C_6H_3$ | $CH_3$ | $C_2H_5$ | 73–76 |
| 3 | 2-$ClC_6H_4$ | $CH_3$ | $CH_3$ | 52–54 |
| 4 | 2,4-$Cl_2C_6H_3$ | i-$C_3H_7$ | $CH_3$ | (Oil) |
| 5 | 2,4-$Cl_2C_6H_3$ | $C_2H_5$ | $CH_3$ | (Oil) |
| 6 | 2,4-$Cl_2C_6H_3$ | n-$C_3H_7$ | $CH_3$ | (Oil) |
| 7 | 2-$ClC_6H_4$ | i-$C_3H_7$ | $CH_3$ | (Oil) |
| 8 | 2,4-$Cl_2C_6H_3$ | $CH_2CH=CH_2$ | $CH_3$ | (Oil) |
| 9 | 2,5-$Cl_2C_6H_3$ | $CH_3$ | $CH_3$ | 83–85 |
| 10 | 4-$ClC_6H_4$ | i-$C_3H_7$ | $CH_3$ | 72–73 |
| 11 | 4-Cl—2-$NO_2C_6H_3$ | $CH_3$ | $CH_3$ | 89–90 |
| 12 | 2-$CH_3C_6H_4$ | $CH_3$ | $CH_3$ | (Oil) |
| 13 | 2-$CF_3C_6H_4$ | $CH_3$ | $CH_3$ | (Oil) |
| 14 | 2,4-$F_2C_6H_3$ | $CH_3$ | $CH_3$ | (Oil) |

TABLE I-continued

| 15 | 2-Furyl | n-C₃H₇ | CH₃ | (Oil) |
|---|---|---|---|---|
| 16 | 2,4-Cl₂C₆H₃ | n-C₄H₉ | CH₃ | (Oil) |
| 17 | 2,4-Cl₂C₆H₃ | CH₂CH₂OCH₃ | CH₃ | (Oil) |
| 18 | 2,4-Cl₂C₆H₃ | Cyclohexyl | CH₃ | (Oil) |
| 19 | 2,4-Cl₂C₆H₃ | CH₂CH(CH₃)₂ | CH₃ | (Oil) |
| 20 | 4-Cl—2-CH₃OC₆H₃ | CH₃ | CH₃ | (Oil) |
| 21 | 4-Cl—2-CH₃OC₆H₃ | n-C₃H₇ | CH₃ | (Oil) |
| 22 | 2,4-Cl₂C₆H₃ | CH₂C≡CH | CH₃ | 118-120 |
| 23 | 2,4-Cl₂C₆H₃ | Cyclopropyl | CH₃ | (Oil) |
| 24 | 2,4-Cl₂C₆H₃ | CH₂C(CH₃)₃ | CH₃ | (Oil) |
| 25 | 2,4-Cl₂C₆H₃ | CH(CH)₃CH₂CH₃ | CH₃ | (Oil) |
| 26 | 2,4-Cl₂C₆H₃ | n-C₅H₁₁ | CH₃ | (Oil) |
| 27 | 2,4-Cl₂C₆H₃ | CH(CH₃)CH(CH₃)₂ | CH₃ | (Oil) |
| 28 | 2,4-Cl₂C₆H₃ | Cyclopentyl | CH₃ | (Oil) |
| 29 | 2,5-Cl₂C₆H₃ | n-C₃H₇ | (Oil) | (Oil) |

Footnotes to Table I
Oily products were purified by chromatography on silica.
All ¹H—nmr spectra were measured for CDCl₃ solutions at 20° C. and 100 MHz. The ¹H—nmr spectra of these hindered amides are complex and signals are broadened as the result of rotamers making separate contributions (see Example 1). The numbers used below for the compounds refer to the numbers used in Table I therefor.

4. δ 0.8–1.4 (m,br) and 1.5 (d,br) together = 6H, 3.29–3.6 (m,br,3H), 5.45 (s,br) and 6.98 (s,br) together = 1H, 7.2–8.7 (m,7H).
5. δ 0.75–1.3 (m,br,3H), 2.7–3.2 (m,2H), 3.31 (s) and 3.42 (s) together = 3H, 5.6 (s,br) and 7.01 (s) together = 1H, 7.2–8.8 (m,7H).
6. δ 0.42 (t,br,3H), 0.6–1.0 (m,br,2H), 2.6–3.2 (m,2H), 3.3 (s) and 3.42 (s) and 3.6 (s) together = 3H, 5.5 (d, br) and 7.0 (s) together = 1H, 7.2–8.8 (m,7H).
7. δ 1.18 (dd) and 1.5 (d) together = 6H, 3.2–3.6 (d and m, 4H), 5.45 (d) and 7.0 (s,br) together = 1H, 7.3–8.8 (m,8H).
8. δ 3.3–3.7 (s and m,5H), 4.2–5.8 (m,br) and 7.01 (s) together = 4H, 7.2–8.8 (m,7H).
12. δ 2.35 (s,3H), 2.45 (s) and 2.9 (s) together = 3H, 3.3 (s,br) and 3.6 (s) together = 3H, 5.7 (s,br) and 7.1 (s) together = 1H, 7.2–8.8 (m,8H).
13. δ 2.45 (s,3H), 3.81 (s,3H), 7.1 (s,1H), 7.2–8.8 (m,8H).
14. δ 2.57 (d) and 2.85 (s) together = 3H, 3.35 (s) and 3.57 (s) together = 3H, 5.7 (s,br) and 6.8–8.8 (m) together = 8H.
15. δ 0.72 (t,3H), 1.3 (m,2H), 3.2 (m) and 3.46 (s) together = 5H, 6.55 (m,1H), 6.75 (s,br,1H), 7.1–8.8 (m,6H).
16. δ 0.4–.8 (m,7H), 2.6–3.2 (m) and 3.3 (s) and 3.43 (s) and 3.6 (s) together = 5H, 5.5 (d,br) and 7.0 (s) together = 1H, 7.2–8.8 (m,7H).
17. δ 2.6–3.6 (m) and 3.55 (s) together = 10 H, 5.55 (s,br) and 6.95 (s,br) together = 1H, 7.1–8.8 (m,7H).
18. δ 0.6–1.9 (m,10 H), 2.1–2.7 (m,1H), 2.9–3.7 (m,3H), 5.5 (s,br) and 7.05 (s,br) together = 1H, 7.8–8.8 (m,7H).
19. δ 0.3–0.9 (m,6H), 1.8 (m,1H), 2.5–3.5 (m) and 3.65 (s) together = 5H, 5.5 (d,br) and 7.0 (s,br) together = 1H, 7.2–8.8 (m,7H).
20. δ 2.05 (s,br) and 2.45 (s) and 2.8 (s) and 3.3 (s,br) and 3.55 (s) and 3.7 (s,br) and 3.85 (s) together = 9H, 5.6 (s) and 6.9–8.8 (m) together = 8H.
21. δ 0.4 (t) and 0.8 (t) together = 3H, 1.5 (m) and 2.3 (m) together = 2H, 2.6–3.2 (m) and 3.2–3.4 (m) and 3.6 (s) and 3.75 (s) and 3.85 (s) together = 8H, 5.6 (s) and 6.8–8.8 (m) together = 8H.
23. δ 0.2–0.4 (m,3H), 1.05 (m,1H), 2.1 (m,1H), 3.55 (s,3H), 6.9 (s,1H), 7.2–8.8 (m,7H).
24. δ 0.6–0.9 (m,9H), 2.6 (s,br) and 2.8 (s,br) and 3.15 (s,br) and 3.4 (s,br) and 3.5 (s,br) and 3.7 (s,br) together = 5H, 5.6 (d,br) and 7.2–8.8 (m) together = 7H.
25. δ 0.4–2.3 (m,8H), 3.0–3.6 (m) and 3.3 (s) and 3.45 (s) and 3.85 (s) together = 4H, 5.5 (d,br) and 7.0 (m) together = 1H, 7.2–8.8 (m,7H).
26. δ 0.6–1.4 (m,9H), 2.9 (m) and 3.3 (s) and 3.5 (s) and 3.62 (s) together = 5H, 5.5 (d,br) and 7.05 (s) together = 1H, 7.2–8.8 (m,7H).
27. δ 0.4–1.6 (m,10 H), 2.1–3.5 (m) and 3.67 (s) together = 4H, 5.2 (dd,br,1H), 7.0–8.8 (m,7H).
28. δ 1.1–2.6 (m,8H), 3.3–3.7 (m) and 3.45 (s) and 3.5

TABLE I-continued (s) together = 4H, 5.55 (s,br) and 7.1–8.8 (m) together = 8H.
29. δ 0.5 (t) and 0.8–1.8 (m) together = 5H, 2.7–3.0 (m,2H), 3.35 (s) and 3.4 (s) and 3.05 (s) together = 3H, 5.5 (d,br) and 7.0 (s) together = 1H, 7.2–8.8 (m,7H).

The following, schematically-represented, process steps may be used to prepare the compounds of the invention.

STEP 1

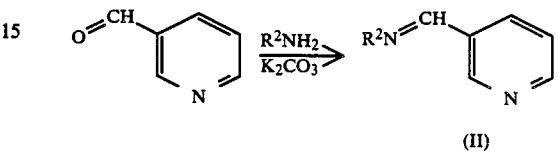

(II)

STEP 2

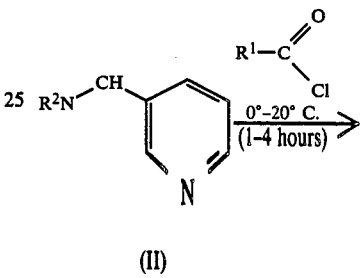

(II)

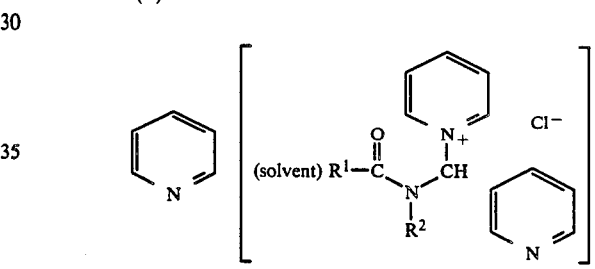

not isolated (III)

STEP 3

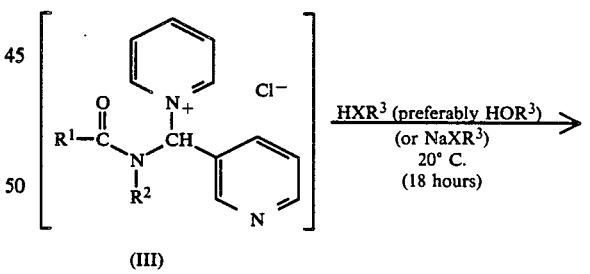

(III)

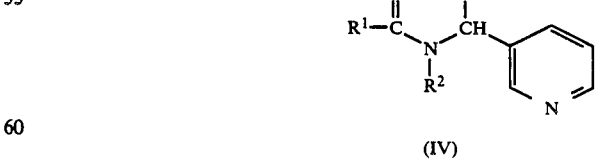

(IV)

The preparation of the imine (II) may follow standard procedures whilst Steps 2 and 3 can be conducted as a 'one-pot', operation since the pyridinium species (III) is generated and used in situ. The overall sequence of the entire process (i.e. all steps) is very simple and the reactions take place at room temperature, or below. The nucleophile $^-XR^3$ (preferably $^-OR^3$) may be used per se as $HXR^3$ (preferably $HOR^3$), or as its salt, particularly for dithiocarbamates i.e. wherein $XR^3$ is $SCSNR^5R^6$.

The compounds of formula I, and compositions containing them, are variously active against a wide range of fungal diseases, particularly, for example, against:

*Plasmopara viticola* (downy mildew) on vines and
*Phytophthora infestans* (late blight) on potatoes and tomatoes and other species of Phytophthora.
Other downy mildews, powdery mildews and other fungal and bacterial diseases, for example:
*Venturia inaequalis* (scab) on apples
*Pyricularia oryzae* on rice
*Cercospora arachidicola* on peanuts and other Cercospora species.
*Erysiphe graminis* on barley.
*Uncinula necator* on vines.
*Podosphaera leucotricha* on apples and other powdery mildews.
*Xanthomona oryzae* on rice.
Some of the compounds have also shown a broad range of activities against fungi in vitro. They have activity against various pathogens which cause post-harvest diseases of fruit (e.g. *Penicillium digatatum* and *italicum* on oranges and *Gloeosporium musarum* on bananas).

The compounds can move acropetally in the plant tissue.

The compounds may be used as such for fungicidal purposes but are more conveniently formulated into compositions for such usage. The invention thus provides a fungicidal composition comprising a compound of general formula (I) as hereinbefore defined, and, optionally, a carrier or diluent.

The invention also provides a method of combating fungi, which comprises applying to a plant, to seed of a plant, or to the locus of the plant or seed, a compound, or a composition as hereinbefore defined.

The compounds also display plant growth regulating properties.

The plant growth regulating effects of the compounds are manifested as, for example, by a retardation or dwarfing effect on the vegetative growth of woody and herbaceous mono- and di-cotyledonous plants. Such retardation or dwarfing may be useful, for example, in peanuts, cereals (such as wheat, barley and rice), oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The retardation of woody species is useful in controlling of the growth of trees under power lines etc. The growth of trees acting as windbreaks, for example in orchards, may be controlled to prevent the need for excessive cutting back of foliage. Control of the growth of conifers may be useful in plantation management. Compounds which induce retardation or dwarfing may also be useful in modifying the stem growth of sugar cane thereby increasing the concentration of sugar in the cane at harvest; in sugar cane, the flowering and ripening may be controllable by applying the compounds. Retardation of peanuts can assist in harvesting. Growth retardation of grasses can help maintenance of grass swards. Examples of suitable grasses are *Strenotaphrum secundatum* (St. Augustine grass), *Cynosurus cristatus*, *Lolium multiflorum* and *perenne*, *Agrostis tenuis*, *Cynodon dactylon* (Bermuda grass), *Dactylis glomerata*, *Festuca* spp. (e.g. *Festuca rubra*) and *Poa* spp. (e.g. *Poa pratense*). The compounds may retard grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also retard weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grassover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturising ornamental, household, garden and nursery plants (e.g. poinsettias, roses, chrysanthemums, carnations, tulips and daffodils).

As indicated above, the compounds can also be used to retard woody species. This property can be used to control hedgerows or to shape or reduce the need for pruning, of fruit trees (e.g. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g. rice), the number of flowering shoots per unit area may be increased thereby increasing the overall grain yield of such crops. In addition better control and modification of hierarchical relationships is possible both in vegetative and reproductive stages of monocotyledonous and, more especially, of dicotyledenous plant growth, whereby the number of flowering shoots per unit area may be modified in such a way as to increase yield. In the treatment of rice plants, or rice crops the invention compounds can be applied, e.g. as granules or a granular formulation, for example as slow release granules, to nursery boxes, paddy water and other like cultivation loci and media. Paddy rice may be treated by submerged application of granules. In grass swards, especially amenity grass, an increase in tillering could lead to a denser sward which may result in increased resilience in wear; and to increased yields and better quality of forage grass, e.g. improved digestibility and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (i.e. the harvested yield as a proportion of the total dry matter produced) by altering dry matter partitioning. This applies to all the aforementioned root, pod, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds may have a growth stimulating effect on plants.

It is to be understood that not all the compounds of the present invention will necessarily show all the above mentioned plant growth regulating effects. There may be advantages in compounds which have a broad spectrum of plant growth regulating effects against a wide range of species. However, equally useful are compounds which have a high specific activity with respect to a particular species and/or plant growth regulating effect.

The Examples show that the compounds of the present invention are generally very effective as growth retardants on a range of species, especially on maize and dicotyledonous species such as apples. The compounds generally show excellent reduction of interligular length, which is one indication of internode length reduction in mature plants. On woody species such as apples the compounds act as general retardants providing scope for their use as field management aids. The compounds generally have a substantial green up effect associated with the activity and in cereals can influence tillering which may be lead to increased ear number at maturity and hence increases in yield. Certain of the compounds of the present invention are substantially more active as growth retardants on apples then on wheat, rice and barley. In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of aspecific compound for any specific purpose for which it is suitable.

The compounds may be used as such for fungicidal and plant growth regulating purposes but are more conveniently formulated into compositions for such usage.

The invention thus provides a plant growth regulating composition comprising a compound of general formula (I) as hereinbefore defined, or a salt, ester or metal complex thereof; and, optionally, a carrier or diluent.

The invention also provides a method of regulating plant growth, which comprises applying to the plant, to seed of a plant or to the locus of a plant or seed, a compound, or a salt, ester or metal complex thereof, as hereinbefore defined, or a composition containing the same.

The compounds, salts' metal complexes, and esters can be applied in a number of ways, for example th can beey applied, formulated or unformulated, directly to to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide). The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal activity or plant growth regulating activity, or which possess insecticidal activity.

The other fungicidal compound can be, for example, one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl aluminium, fenarimol, iprodione, procymidione, vinclozolin, penconazole, myclobutanil, R0151297, S3308, pyrazophos, ethirimol, ditalimfos, tridemorph, triforine, nuarimol, triazbutyl, guazatine, propiconazole, prochloraz, flutriafol, chlortriafol i.e. the chemical 1-(1,2,4-triazol-1-yl)-2-(2,4-dichlorophenyl)hexan-2-ol, DPX H6573(1-((bis-4-fluorophenyl)methylsilyl)methyl)-1H-1,2,4-triazole, triadimefon, triadimenol, diclobutrazol, fenpropimorph, fenpropidine, triademorph, imazalil, fenfuram, carboxin, oxycarboxin, methfuroxam, dodemorph, BAS 454, blasticidin S, Kasugamycin, edifenphos, kitazin P, phthalide, probenazole, isoprothiolane, tricyclazole, pyroquilan, chlorbenzthiazone, neoasozin, polyoxin D, validamycin A, repronil, flutolanil, pencycuron, diclomezine, phenazin oxide, nickel dimethyldithiocarbamate, techlofthalam, bitertanol, bupirimate, etaconazole, streptomycin, cypofuram, biloxazol, quinomethionate, dimethirimol, fenapanil, tolclofos-methyl, pyroxyfur, polyram, maneb, mancozeb, captafol, chlorothalonil, anilazine, thiram, captan, folpet, zineb, propineb, sulphur, dinocap, binapacryl, nitrothal-isopropyl, dodine, dithianon, fentin hydroxide, fentin acetate, tecnazene, quintozene, dichloran, copper containing compounds such as copper oxychloride, copper sulphate and Bordeaux mixture, and organomercury compounds such as 1-(2-cyano-2-methoxyimino-acetyl)-3-ethyl urea.

The compounds of general formula (I) can be mixed with soil, peat or other rooting media for the protection of plants against seed-borne, soil-borne or foliar fungal diseases.

Suitable insecticides are pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

The other, additional plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides.

Examples of suitable plant growth regulating compounds, which can display synergy in admixture, or use, with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, technazene, fluoridamid, mefluidide, substituted quaternary ammonium and phosphonium compounds (e.g. chlormequat*, chlorphonium, phosphon D, or mepiquat), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat*, benzoylpropethyl, 3,6-dichloropicolinic acid, uniconazole, triapenthanol, flurpirimidol, paclobutrazol, tetcyclacis and amidichlor. Synergy will be most likely to occur with those of the foregoing which are quaternary ammonium compounds; and, in particular, those marked with an asterisk.

The following Examples illustrate the invention; the temperatures are given in degrees Centrigrade (°C.).

EXAMPLE 1

This Example illustrates the preparation of Compound No 1 of Table 1.

STEP 1: Preparation of the imine

To a stirred solution of methylamine (23.25 g) in ethanol (225 ml) containing finely ground anhydrous potassium carbonate (103.5 g) was added pyridine-3-carboxaldehyde (80.25 g) at such a rate that the temperature of the reaction did not exceed 25°. Following the addition the mixture was kept at room temperature for 20 hours, when it was filtered and the solvent removed under reduced pressure. The pale orange oil was taken up in n-hexane (200 ml), filtered to remove a small quantity of insoluble material and then evaporated under reduced pressure. Distillation of the residue gave the imine (82.2 g; 91%) as a colourless mobile oil, b.p. 64°–65°/0.06 mm.

STEP 2 and 3: Preparation of the Title Compound

To a solution of the foregoing imine (1.0 g) in anhydrous pyridine (8 ml) was added 2,4-dichlorobenzoyl chloride (1.75 g) dropwise and with stirring at such a rate that the temperature of the reaction did not exceed 5° with ice-bath cooling. Following the addition the mixture was allowed to come to room temperature with stirring when it was kept for a further 30 min. before anhydrous methanol (8 ml) was added. The mixture was kept at room temperature for 18 hours, poured into water and extracted with ether (2×25 ml). The combined extracts were dried (MgSO$_4$) and then evaporated to give a thick pale yellow oil. This solidified when treated with ether-n-hexane at −78° and the product so obtained recrystallised from n-hexane. There was obtained 1.00 g of product, m.p. 68°–71°.

Found: C, 55.65; H, 4.31; N, 8.67. $C_{15}H_{14}Cl_2N_2O_2$ requires: C, 55.38; H, 4.31, N, 8.61%.

The 'H-nmr spectra of these hindered amides is complex as the result of rotamers contributing different signals. The relative proportion and life-time of the rotamers is dependant both upon the structure of each individual compound as well as the temperature at which the spectrum is measured. There are two principle rotamers (A and B, below; only one enantiomer shown) each of which resolve into two further rotamers (observed at −50° C.) about the torsion axis (provided the aryl ring is unsymmetrically substituted about the torsion axis).

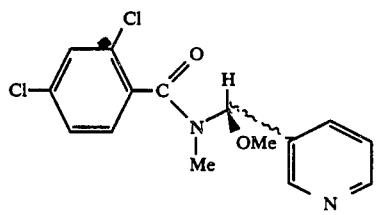

(A)

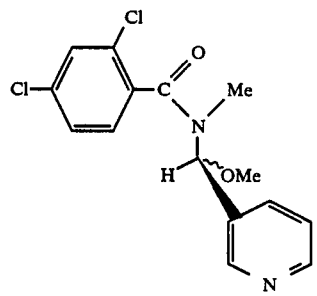

(B)

(N.B. Me represents $CH_3$ and OMe represents $OCH_3$).

Thus the 'H-nmr spectrum for the compound measured at 20°, 100 MHz, (CDCl$_3$) is as follows: 2.6 (s, 3H, NMe, A), 2.9 (d, broad, 3H, NMe, B) 3.4 (d, broad, 3H, OMe, B), 3.61 (s, 3H, OMe, A), 5.6 (s, broad, 1H, —CH, B), 7.0 (s, 1H, —CH, A), 7.3–8.8 (m, 7H, aryl and phenyl protons, A+B).

A:B=9:2.

EXAMPLE 2

An emulsifiable concentrate was made up by mixing the ingredients, and stirring the mixture until all the constituents were dissolved.

| | |
|---|---|
| Compound of Example 1 | 10% |
| Ethylene dichloride | 40% |
| Calcium dodecylbenzenesulphate | 5% |
| "Lubrol" L | 10% |
| "Aromasol" H | 35% |

EXAMPLE 3

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44-100, to obtain the desired size of grains.

| | |
|---|---|
| Compound of Example 1 | 50% |
| "Dispersol" T | 25% |
| "Lubrol" APN5 | 1.5% |
| Sodium acetate | 23.5% |

EXAMPLE 4

The ingredients were all ground together to produce a powder formulation readily dispersible in liquids.

| | |
|---|---|
| Compound of Example 1 | 45% |
| "Dispersol" T | 5% |
| "Lissapol" NX | 0.5% |
| "Cellofas" B600 | 2% |
| Sodium acetate | 47.5% |

EXAMPLE 5

The active ingredient was dissolved in a solvent and the resultant liquid was sprayed on to the granules of China clay. The solvent was then allowed to evaporate to produce a granular composition.

| | |
|---|---|
| Compound of Example 1 | 5% |
| China clay granules | 95% |

EXAMPLE 6

A composition suitable for use as a seed dressing was prepared by mixing the three ingredients.

| | |
|---|---|
| Compound of Example 1 | 50% |
| Mineral oil | 2% |
| China clay | 48% |

EXAMPLE 7

A dusting powder was prepared by mixing the active ingredient with talc.

| | |
|---|---|
| Compound of Example 1 | 5% |
| Talc | 95% |

EXAMPLE 8

A Col formulation was prepared by ball-milling the constituents set out below and then forming an aqueous suspension of the ground mixture with water.

| | |
|---|---|
| Compound of Example 1 | 40% |
| "Dispersol" T | 10% |
| "Lubrol" APN5 | 1% |
| Water | |

EXAMPLE 9

A dispersible powder formulation was made by mixing together the ingredients set out below and then grinding the mixture until all were thoroughly mixed.

| | |
|---|---|
| Compound of Example 1 | 25% |
| "Aerosol" OT/B | 2% |
| "Dispersol" A.C. | 5% |
| China clay | 28% |
| Silica | 40% |

EXAMPLE 10

This Example illustrates the preparation of a dispersible powder formulation. The ingredients were mixed and the mixture then ground in a comminution mill.

| | |
|---|---|
| Compound of Example 1 | 25% |
| "Perminal" BX | 1% |
| "Dispersol" T | 5% |
| Polyvinylpyrrolidone | 10% |
| Silica | 25% |
| China clay | 34% |

EXAMPLE 11

The ingredients set out below were formulated into a dispersible powder by mixing then grinding the ingredients.

| | |
|---|---|
| Compound of Example 1 | 25% |
| "Aerosol" OT/B | 2% |
| "Dispersol" A | 5% |
| China clay | 68% |

In Examples 2 to 11 the proportions of the ingredients given are by weight. The remaining compounds of Table I were all similarly formulated as per Examples 2 to 11.

There now follows an explanation of the compositions or substances represented by the various Trade Marks and Trade Names mentioned above.

| | |
|---|---|
| LUBROL L: | a condensate of nonyl phenol (1 mole) with ethylene oxide (13 moles) |
| AROMASOL H: | a solvent mixture of alkylbenzenes |
| DISPERSOL T & AC: | a mixture of sodium sulphate and a condensate of formaldehyde with sodium naphthalene sulphonate |
| LUBROL APN5: | a condensate of nonyl phenol (1 mole) with naphthalene oxide (5.5 moles) |
| CELLOFAS B600: | a sodium carboxymethyl cellulose thickener |
| LISSAPOL NX: | a condensate of nonyl phenol |

| | |
|---|---|
| | (1 mole) with ethylene oxide (8 moles) |
| AEROSOL OT/B: | dioctyl sodium sulphosuccinate |
| PERMINAL BX: | a sodium alkyl naphthalene sulphonate |

Disease control was recorded using the following grading system:

4=no disease
3=trace to 5% of disease on untreated plants
2=6-25% of disease on untreated plants
1=26-59% of disease on untreated plants
0=60-100% of disease on untreated plants The results are shown in Table II.

TABLE II

| COMPOUND NUMBER | PUCCINIA RECONDITA (WHEAT) | ERYSIPHE GRAMINIS (BARLEY) | VENTURIA INAEQUALIS (APPLES) | CERCOSPORA ARACHIDICOLA (PEANUTS) |
|---|---|---|---|---|
| 1 | 0 | 4 | 0 | 3 |
| 2 | 0 | 4 | 0 | 0 |
| 3 | 0 | 4 | 0 | 0 |
| 4 | 0 | 4 | 0 | 2 |
| 5 | 0 | 4 | 4 | 2 |
| 6 | 0 | 4 | 4 | 1 |
| 7 | 0 | 4 | 4 | 1 |
| 8 | — | 4 | — | 0 |
| 9 | 0 | 4 | 0 | 2 |
| 10 | 0 | 4 | 0 | 0 |
| 11 | 0 | 3 | 0 | 1 |
| 12 | 0 | 4 | 0 | 0 |
| 13 | 0 | 4 | 0 | 3 |
| 14 | 0 | 4 | 0 | 0 |
| 15 | 0 | 4 | 0 | 0 |
| 16 | 2 | 4 | — | 0 |
| 17 | 2 | 4 | 4 | 1 |
| 18 | 4 | 4 | 4 | 3 |
| 19 | 3 | 4 | 0 | 2 |
| 20 | 0 | 4 | 0 | 0 |
| 21 | 0 | 4 | 0 | 2 |
| 22 | 0 | 4 | 3 | 4 |
| 23 | 0 | 2 | 0 | 0 |
| 24 | 4 | 4 | 3 | 4 |
| 25 | 0 | 4 | 3 | 0 |
| 26 | 0 | 4 | 4 | 0 |
| 27 | 3 | 4 | — | — |
| 29 | 0 | 4 | 3 | 4 |

EXAMPLE 12

The compounds were tested against a variety of mainly foliar fungal diseases of plants. The techniques employed were as follows.

For all tests the plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. The solutions or suspensions (100 ppm ai.) were sprayed on the foliage and applied to the roots of the plant via the soil. The sprays were applied to maximum retention and the root drenches to a final concentration equivalent to approximately 40 ppm ai./dry soil. Tween 20, to give a final concentration of 0.05%, was added when the sprays were applied to cereals. (a.i. means "active ingredient").

Most were protectant tests where the compound was applied to the soil and roots and to the foliage one or two days before the plant was inoculated with the pathogen. The foliar pathogens were applied by spraying as spore suspensions onto the leaves of the test plants.

After inoculation, the plants were placed in an appropriate environment to allow infection to proceed and then incubated until the disease was ready for assessment. The period between inoculation and assessment varied from four to fourteen days according to the disease and the environment.

EXAMPLE 13

Whole Plant Screen

Compound numbers 4, 6, 7, 12, 16, 17, 18, 19 and 29 were tested on a whole plant screen. The compounds were tested for plant growth regulator activity against five species for various growth effects relevant to plant growth regulation.

Methodology

The plant species used in this screen are presented in Table II with the leaf stage at which they were sprayed. Each chemical was applied at 4000 ppm (4kg/ha in a 1000 1/ha field volume) using a tracksprayer and a SS8004E (Teejet) nozzle.

After spray the plants were grown in a glasshouse with 25° C. day/22° C. night temperatures. The exception to this were the temperate cereals, wheat and barley which are grown in 13°-16° C. day/11°-13° C. night temperatures. Supplementary lighting was supplied when necessary to provide an average photoperiod of 16 hours (14 hours minimum).

After 2-6 weeks in the glasshouse, depending on species and time of year, the plants were visually assessed for morphological characteristics. Formulation blanks were used as controls to assess the plants against. The results are presented in Table III.

TABLE III

| PLANT MATERIAL USED FOR WHOLE PLANT SCREEN |
|---|
| Growth Stage   No. Plants   Compost |

TABLE III-continued

| Species | Code | Variety | at Treatment | per 3" Pot | Type |
|---|---|---|---|---|---|
| Barley | BR | Atem | 1–1.5 leaves | 4 | JIP* |
| Wheat | WW | Timmo | 1–1.5 leaves | 4 | JIP |
| Maize | MZ | Earliking | 2¼–2½ leaves | 1 | PEAT |
| Apple | AP | Red Delicious | 4–5 leaves | 1 | JIP |
| Rice | RC | Ishikari | 2–2½ leaves | 4 | JIP |

| SPECIES | COMPOUND NO. | R | I | T | G |
|---|---|---|---|---|---|
| WHEAT | 4 |   |   | 1 |   |
|   | 6 |   |   |   |   |
|   | 7 |   |   |   |   |
|   | 12 |   |   |   |   |
|   | 16 |   |   |   |   |
|   | 17 |   |   | 1 |   |
|   | 18 |   |   |   |   |
|   | 19 |   |   |   |   |
|   | 29 |   |   |   |   |
| BARLEY | 4 |   |   |   |   |
|   | 6 |   |   | 1 |   |
|   | 7 | 1 |   |   |   |
|   | 12 | 1 |   |   |   |
|   | 16 |   |   |   |   |
|   | 17 | 1 |   |   |   |
|   | 18 |   |   |   |   |
|   | 19 |   |   |   |   |
|   | 29 |   |   |   |   |
| RICE | 4 |   |   |   |   |
|   | 6 | 1 |   |   |   |
|   | 7 | 2 | 3 |   |   |
|   | 12 |   |   |   |   |
|   | 16 |   |   |   |   |
|   | 17 |   | 1 |   |   |
|   | 18 |   |   |   |   |
|   | 19 |   |   |   |   |
|   | 29 |   |   | 1 |   |
| APPLES | 4 | 3 | 3 | 3 | 1 |
|   | 6 | 3 | 3 | 2 | 1 |
|   | 7 | 3 | 3 | 2 |   |
|   | 12 |   |   |   |   |
|   | 16 | 3 | 2 | 1 |   |
|   | 17 | 2 | 2 | 1 | 1 |
|   | 18 | 3 | 3 |   | 2 |
|   | 19 | 3 | 3 |   | 2 |
|   | 29 |   |   |   |   |
| MAIZE | 4 |   |   |   |   |
|   | 6 |   |   |   |   |
|   | 7 |   |   |   |   |
|   | 12 |   |   |   |   |
|   | 16 |   |   |   |   |
|   | 17 |   |   |   |   |
|   | 18 |   |   |   |   |
|   | 19 | 2 | 3 |   | 1 |
|   | 29 |   |   |   |   |

JIP* = John Innes Potting Compost.
Key:
R = Retardation
G = Greening effect
T = Tillering or side shooting
I = Interligular or internodal length reduction
All effects are scored visually on a 1–3 basis where
1 = 10–30%
2 = 31–60%
3 = 61–100%
Blank means less than 10% effect.

I claim:

1. A compound having the general formula (I):

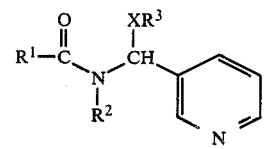

or a stereoisomer thereof, wherein $R^1$ is phenyl, thiophene, furan or pyridine, optionally substituted with halogen, alkoxy, alkyl, trifluoromethyl, nitro or phenyl; $R^2$ is H, $C_{1-6}$ alkyl, $C_{3-6}$ cycloalkyl, $C_{1-6}$ alkoxy $C_{1-6}$ alkyl, alkenyl having from 2 to 6 carbon atoms, or alkynyl having from 2 to 6 carbon atoms; X is O, NH, or S; provided that when X is O, $R^3$ is $C_{1-6}$ alkyl, alkenyl having from 2 to 6 carbon atoms, or alkynyl having from 2 to 6 carbon atoms, or $COR^4$ where $R^4$ is $C_{1-6}$ alkyl, alkenyl having from 2 to 6 carbon atoms or alkynyl having from 2 to 6 carbon atoms; and that when X is NH, $R^3$ is $-CO-C_{1-6}$ alkyl; and that when X is S, $R^3$ is $C_{1-6}$ alkyl, alkenyl having from 2 to 6 carbon atoms or $CSNR^5R^6$ where $R^5$ and $R^6$, which may be the same or different are H, $C_{1-6}$ alkyl or alkenyl having from 2 to 6 carbon atoms; or $XR^3$ together represent $-CN$; or an agronomically acceptable salt or metal complex thereof.

2. A compound having the general formula:

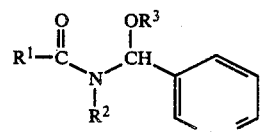

or a stereoisomer wherein $R^1$ is phenyl, thiophene, furan or pyridine, optionally substituted with halogen, alkoxy, alkyl, trifluoromethyl, nitro or phenyl; $R^2$ is $C_{1-6}$ alkyl, $C_{1-6}$ alkoxy-$C_{1-6}$ alkyl, cycloalkyl, alkenyl having from 2 to 6 carbon atoms, or alkynyl having from 2 to 6 carbon atoms; and $R^3$ is $C_{1-3}$ alkyl; or an agronomically acceptable salt or metal complex thereof.

3. A compound as claimed in claim 1 or claim 2 wherein $R^1$ is furyl or phenyl substituted with halogen, nitro, trifluoromethyl or alkoxy; $R^2$ is $C_{1-6}$ alkyl, allyl, methoxyethyl, propargyl, or $C_{3-6}$ cycloalkyl; and $R^3$ is methyl.

4. A compound as claimed in claim 1 wherein $R^1$ is 4-chlorophenyl or 2,4-dichlorophenyl.

5. A fungicidal composition comprising, as an active ingredient, a fungicidally effective amount of a compound as defined in claim 1 together with a carrier or diluent therefor.

6. A method of combating fungi which comprises applying to a plant, to seed of a plant, or to the locus of the plant or seed, a fungicidally effective amount of a compound as defined in claim 1.

* * * * *